United States Patent
Nier et al.

(10) Patent No.: US 6,248,369 B1
(45) Date of Patent: Jun. 19, 2001

(54) WATER TREATMENT PROCESS

(75) Inventors: Thomas J. Nier; Tosby L. Linn, both of Corpus Christi, TX (US)

(73) Assignee: Bay Chemical and Supply Company

( * ) Notice: Subject to any disclaimer, the term of this patent is extended or adjusted under 35 U.S.C. 154(b) by 0 days.

(21) Appl. No.: 09/055,205

(22) Filed: Apr. 6, 1998

Related U.S. Application Data

(62) Division of application No. 08/744,742, filed on Oct. 28, 1996, now abandoned.

(51) Int. Cl.$^7$ .......................... A01N 59/02; A01N 59/06; A01N 59/20; A01N 55/02; C02F 1/56
(52) U.S. Cl. .................. 424/637; 424/630; 424/632; 424/633; 424/634; 424/635; 424/638; 424/646; 424/647; 424/648; 424/682; 424/698; 504/151; 504/152; 514/499; 514/500; 514/502; 210/705; 210/723; 210/724; 210/728; 210/732; 210/735; 210/749; 210/753; 210/764
(58) Field of Search ..................... 424/631–635, 424/637–638, 630, 646–648, 682, 698; 210/705, 723, 728, 735, 724, 732, 749, 753, 764; 514/499, 500, 502; 504/151, 152

(56) References Cited

U.S. PATENT DOCUMENTS

| | | | |
|---|---|---|---|
| 3,461,163 | * 8/1969 | Boothe | 564/296 |
| 3,844,760 | * 10/1974 | Nelson | 504/152 |
| 4,012,221 | * 3/1977 | Walker | 504/151 |
| 4,505,734 | * 3/1985 | Freedenthal | 504/152 |
| 4,588,508 | * 5/1986 | Allenson et al. | 210/708 |
| 4,761,239 | * 8/1988 | Wardell | 210/727 |
| 4,882,070 | * 11/1989 | Wardell | 210/727 |
| 4,923,629 | * 5/1990 | Hasegawa et al. | 252/181 |
| 5,510,108 | * 4/1996 | Chouraqui | 424/408 |
| 5,541,150 | * 7/1996 | Garris | 504/152 |
| 6,120,698 | * 9/2000 | Rounds et al. | 252/181 |

FOREIGN PATENT DOCUMENTS 63-240989 * 10/1988 (JP).

OTHER PUBLICATIONS

Kirk–Othmer Encyclopedia of Chemical Technology, 4$^{th}$ Edition, vol. 11, John Wiley and Sons, New York, pp. 61–67, 1994.*

Algae Control in Water–Supply Reservoirs by C.B. Muchmore, Journal of American Water Works Association, Water Technology/Quality, pp. 273–278, May 1978.*

Controlling Algae in Water Supply Impoundments by R. K. Raman, Journal of American Water Works Association, Management and Operations, pp. 41–43, Aug. 1985.*

Advances in Tast–and–Odor Treatment and Control by I.H. Suffet, Joel Mallevialle, Elizabeth Kawczynski, American Water Works Association Research Foundation, pp. 39–43, 1995.*

Algal Bloom Control Study—Huanjing Kevue Xuebao, China, Yin et al., 1989.*

* cited by examiner

Primary Examiner—John Pak
(74) Attorney, Agent, or Firm—G. Turner Moller

(57) ABSTRACT

A water soluble copper salt, preferably cupric sulfate pentahydrate, is mixed with water. A small quantity of an acidic flocculant is added to the copper sulfate solution to acidify the water and promote dissolving of the copper sulfate in the water. A 25–50% water solution of an acidic flocculant, with or without a cationic polymeric flocculant aid, is prepared and pumped into a processing vessel or tank. The acidified copper sulfate solution is added to the tank and mixed with the acidic flocculant. The algicide-flocculant solution is transported to a municipal water plant and added to raw water in the clarifier to drop out particulates in the incoming water and control algae in the clarifier.

11 Claims, No Drawings

WATER TREATMENT PROCESS

This application is a division of application Ser. No. 08/744,742 filed Oct. 28, 1996 now abandoned.

This invention is a process for treating raw water and producing potable water meeting accepted purity standards.

BACKGROUND OF THE INVENTION

Fresh water from rivers or lakes is treated in a water plant to convert the raw water into water for human consumption meeting accepted purity standards. The processes used have been honed over the years to produce high quality potable water from raw water at surprisingly low costs.

The primary treatment in a water plant occurs in a clarifier where a flocculant is added to raw water. A water plant clarifier is a large sized, round or rectangular concrete structure. The flocculent causes particles suspended in the water to coagulate, subsequently growing in size and weight. The clarifier is sized to provide sufficient residence time for the majority of the solids to drop out of suspension. Water is then passed through sand filters, perhaps treated with activated carbon, chlorinated and possibly fluoridated before being delivered to water supply mains which transport the treated water to residences, businesses and industries.

One of the recurrent problems in water treatment plant operations is the growth of algae in the clarifier and sand filters. Algae come in many types including filamentous algae, such as Cladaphora and Spirogyra, planktonic algae such as Microcystis and Anabaena, branched algae such as Chara vulgaris and Nitellam, swimming pool algae commonly referred to as black, brown and red algae and algae found in ponds such as Dictyosphaerium, Spirogyra, Oedogonium, Chlorococcum, Pithophora, Hyudrodictyon and Lyngbya. It is not uncommon to see a municipal water plant clarifier with a beard of algae around its peripheral walls and filamentous algae growths several feet long.

As used herein, the term municipal water plant is intended to mean a water plant used in treating raw water and converting it to potable water for human consumption, regardless of whether the entity doing so is public or private.

Algae blooms have been noted to appear literally overnight under the right temperature and sunlight conditions and, if left untreated, will cause taste and odor problems in the finished waters. The problems caused by algae in municipal water plants are handled in a variety of ways by current treatment methods. The odor and taste problems which typically recur during periods of high summer temperatures and long daylight hours occur from detritus thrown off by algae in the clarifier. Not all of this detritus is removed by sand filters. Any detritus passing through the sand filters is converted in the final chlorination process to a family of chloro-organic compounds which cause the objectionable smell and taste that consumers complain about.

The standard treatment for controlling algae in municipal water plants is to scatter crystals of cupric sulfate pentahydrate, $CUSO_4.5H_2O$, which is also known by its common name blue vitriol, into the clarifier. Blue vitriol is commercially available in 50 pound bags having crystals ranging in size from fine ($\frac{1}{8}$") to large (1"). Scattering is done with a shovel, a scoop, or by hand. Ideally, the crystals dissolve in the water so the copper ion is present in the water. The soluble or active copper (II) ion kills algae because of its effect on chlorophyll which is a large porphyrin structure occurring either as blue-green chlorophyll-a or yellow-green chlorophyll-b. Both molecules have four centrally placed nitrogen atoms which complex a single magnesium atom. The magnesium removes carbon dioxide from the water and delivers it to the algae thus allowing photosynthetic growth. The soluble copper (II) ion replaces the magnesium by forming a stronger porphyrin complex, which does not bond with carbon dioxide. The algae dies by virtue of its growth mechanism being squelched by a lack of carbon dioxide, in a process analogous to the chemical poisoning of hemoglobin in mammals. A small part of the algicidal copper exits the treated water stream in the clarifier sludge and not with the finished water because it has been intimately bonded to the algae chlorophyll. A large part of the copper sulphate is believed to remain undissolved and drops into the clarifier sludge as copper hydroxide coated pellets. One of the inherent advantages of copper algicides is that algae cannot mutate or evolve to avoid its effect. No amount of evolution can prevent copper from displacing magnesium in the chlorophyll and no amount of evolution can cause the copper porphyrin to absorb carbon dioxide.

Disclosures of some interest are found in U.S. Pat. Nos. 3,844,760; 4,012,221; 4,505,734 and 5,541,150.

SUMMARY OF THE INVENTION

The above description of the prior art is an idealized situation but which has a number of practical problems and disadvantages, some subtle and some not so subtle. A substantial part of the blue vitriol does not dissolve because it is difficult to dissolve in water which is not acidic. Plainly put, blue vitriol crystals do not dissolve very well in pH 7, or more alkaline, water. Thus, much of the copper sulfate is wasted because it ends up in the clarifier sludge as blue vitriol pebbles with a thin copper hydroxide coating. In addition, scattering blue vitriol crystals in the clarifier does not produce uniform dosages of copper sulfate in the water. Instead, very high dosages will be found immediately down current from the crystals and little copper sulfate will be found elsewhere.

In this invention, a water soluble copper salt is dissolved in an aqueous solution of an acidic flocculant. It is fortuitous that the selected flocculants are quite acidic because many water soluble copper salts, and the preferred copper sulfate, are much more soluble in low pH water than in neutral to high pH water. The resultant algicide-flocculant solution is commonly delivered in a tank truck or by a tank rail car and off loaded into storage tanks.

The solution is then metered into the clarifier, thus delivering a reliable, predictable quantity of flocculant and copper algicide. This technique operates to deliver a uniform low dose of copper algicide in a very simple, efficient and trouble free manner because flocculant metering pumps deliver a controlled amount of flocculant in a manner which mixes the flocculant into the raw water in a thorough and uniform manner. It is this liquid injection that thoroughly and uniformly mixes the algicide with the water, as contrasted to the prior art technique scattering of blue vitriol crystals with a shovel into the clarifier. Efficient mixing of the copper algicide with the water provides low, uniform dosages of copper which is very desirable because little copper is wasted.

The copper solution provides copper (II) ions that displace the magnesium ion in chlorophyll to kill the algae in the clarifier. The amount of copper in the algicide-flocculant solution is controlled; thus the amount of copper in the clarifier is also controlled and is maintained at low levels. The copper reacts with the magnesium in the chlorophyll molecules and, along with the dead algae, collects in the sludge in the bottom of the clarifier.

When using this invention, no blue copper crystals will be found in the clarifier sludge which means that more of the copper has been put to its intended use of killing algae rather than wasted in the clarifier sludge. In addition, the amount of soluble copper ion passing through the clarifier into the finished water will normally not exceed 0.1 ppm which is well below the 1.3 ppm standard required by the Lead and Copper Rule of the Environmental Protection Agency.

It is difficult to overstate the importance of low, uniform dosages of copper. For the algicide to be effective, copper (II) ions must come intimately close to the magnesium ion in the chlorophyll complex of substantially all of the algae cells. Although there is moderate circulation in the clarifier, it is hard to imagine copper ions in concentrations on the order of less than 1 ppm reacting with enough magnesium atoms in chlorophyll to control an algae bloom. However, this can be done with improved mixing and distribution of the algicide when it is combined with the flocculant as in this invention. Uniform dosages are the key to effectiveness. Low dosages are the key to economy.

In the past, a water plant has typically used a conventional flocculant, either with or without a polymeric flocculent aid. With the onset of a substantial algae bloom, attempts would be made to control the algae bloom using the prior art technique with less than satisfactory results. When facing a full grown algae bloom, the amount of copper in the algicide-flocculant solution of this invention would be at a relatively high level which will bring the algae bloom under control in a fairly short period. After the algae bloom is brought under control, the amount of soluble algicide will be reduced in subsequent batches of algicide-flocculant solutions and ultimately reduced to a lower level that is sufficient to keep algae growth suppressed at a very reasonable cost. A large proportion of the algicidal copper exits the treated water stream in the clarifier sludge and not with the finished water because it has been intimately bonded to the algae chlorophyll.

An object of this invention is to provide an improved technique for treating algae in a municipal water plant.

Another object of this invention is to provide an improved technique for preparing an algicide-flocculant solution.

A more specific object of this invention is to treat raw water with an algicide-flocculant solution which, when added to a water plant clarifier, drops particulates out of suspension and simultaneously controls algae in the clarifier.

These and other objects and advantages of this invention will become more apparent as this description proceeds, reference being made to the appended claims.

DETAILED DESCRIPTION

The copper algicide of this invention is selected from water soluble copper salts. From a simple algicidal standpoint, almost any water soluble copper salt is suitable. From the standpoint of producing potable water, the choice is more limited because not all water soluble copper salts can economically be put into drinking water. Thus, the common choices for the water soluble copper salt are copper sulfate, copper chloride, copper nitrate and copper acetate. The selection will likely be based on the relative cost of copper salts. Copper sulfate is the preferred water soluble copper salt because it is the only one presently approved for use in municipal water plants; it is effective as a source of copper (II) ions; and, it is the least expensive of the possible candidates. The preferred form of copper sulfate is blue vitriol which is cupric sulfate pentahydrate.

The amount of blue vitriol in the algicide-flocculant solution varies between 0.1–5% by weight. The proportion of copper in blue vitriol is 25.45% by weight which means that the copper concentration in the algicide-flocculant solution varies from about 0.025–1.25%. Preferably, the amount of blue vitriol in the algicide-flocculant solution is 0.1–1% by weight meaning that the active copper concentration in the preferred solution is 0.025–0.25% by weight. The equivalent concentration of other soluble copper salts is found in Table I:

TABLE I

| copper salt | copper salt concentration necessary to produce 0.025% active Cu (II) | copper salt concentration necessary to produce 1.25% active Cu (II) |
| --- | --- | --- |
| $CUSO_4.5H_2O$ | 0.10% | 5.0% |
| $CuCl_2.2H_2O$ | 0.067% | 3.35% |
| $Cu(acetate)_2.H_2O$ | 0.078% | 3.93% |
| $Cu(NO_3)_2.3H_2O$ | 0.095% | 4.75% |
| $Cu(NO_3)_2.6H_2O$ | 0.116% | 5.82% |
| $CUSO_4.H_2O$ | 0.070% | 3.49% |

Accordingly, the concentration of the copper salts vary from about 0.05% to about 6% in order to provide the desired range of active copper concentration.

It has been found that an active copper concentration of 0.25% in the algicide-flocculant solution is sufficient to bring algae blooms under control. As initial batches of algicide-flocculant solution are used in response to an algae bloom, the algae die off substantially. Subsequent batches of algicide-flocculant solution preferably contain reduced amounts of active copper algicide, usually about half the initial dose. It has been found that copper concentrations in the algicide-flocculant solution approaching 0.025%, such as in the range of about 0.025–0.050%, are sufficient as a maintenance dose to keep algae under control and prevent the formation of algae blooms, even under the most trying conditions of temperature and sunlight.

Theoretically, it is possible to add copper salt crystals in the proper proportion to an acidic flocculant solution and agitate the solution to dissolve the copper salt. In practice, this has not been efficient for a variety of reasons. The source of blue vitriol is solid pebbles which require vigorous agitation to dissolve, such as occurs with a powered impeller. With aluminum sulfate as the flocculant, solubility is adversely affected by the common ion effect. It is accordingly much better to dissolve the copper salt in water and then mix the water soluble copper salt solution with the flocculent solution. Using copper sulfate as the algicide, one part blue vitriol is dissolved in two parts water making a nearly saturated copper sulfate solution.

To prepare the water solution of the copper salt, a mixing tank is partially filled with water and a suitable mixer, such as a powered impeller, is used to agitate the water. Preferably, the water is heated with a suitable heater, such as an electrically powered immersion heater or preheated with a conventional water heater. The selected copper salt is taken from commercially available bags and the desired quantity added to the tank. Using blue vitriol, the water solution will initially be bluish but somewhat milky which is caused by partial formation of copper hydroxide. Continued stirring and complete dissolving of the blue vitriol will result in a clear blue color typical of copper sulfate solutions.

During the mixing process, a small quantity of acidic flocculant solution is poured into the tank to acidify the copper salt solution to a pH of no more than 5 and preferably in the range of 4–5. A typical flocculant solution has a pH of about 2.5, which is about the same as lemon juice. Acidifying the solution prevents the formation of copper hydroxide so the copper salt completely dissolves, and remains in solution. Acidifying the solution with the flocculent material avoids using a different acid material which, in the treatment of water for human consumption, might provide regulatory problems.

The flocculant of this invention is acidic and, when mixed with the algicide, acidifies the water used to dissolve the copper salt. Suitable flocculants are aluminum sulfate, iron sulfate, iron chloride and mixtures thereof. Preferably, but not necessarily, the flocculants are prepared in a nearly saturated solution. In a typical process, aluminum oxide is reacted with sulfuric acid to produce liquid aluminum sulfate, i.e. about 47–50% by weight aluminum sulfate in water. Iron sulfate or iron chloride may be prepared by commonly known procedures, as is well known in the art. In this invention, the amount of flocculant in the algicide-flocculant solution varies between 25–50% by weight and preferably is 35–50% by weight.

The invention is also useable with polymer flocculant aids of any suitable type. Polymer flocculant aids are long chain, high molecular weight cationic materials, usually having molecular weights in the range of 100,000–800,000. Conventional flocculants, such as aluminum sulfate, iron sulfate, iron chloride and mixtures thereof, produce relatively small flocs which require relatively long residence times to settle out by gravity in the clarifier. The polymer flocculant aids cause these small flocs to agglomerate into larger particles that settle at faster rates, thereby allowing shorter residence times in the clarifier. The present standard polymer flocculant aids are high molecular weight quaternary amines such as diallyldimethylammonium chloride which is commercially available from CPS Chemical Company, West Memphis, Arkansas. In this invention, the amount of polymer flocculant aid in the algicide-flocculant solution varies between 0–10% by weight but preferably is 0–5% by weight. Preferably, the polymer flocculant aid is added to the flocculant prior to the addition of the water soluble copper salt solution.

Potable water treatment chemicals are typically delivered by tank truck to the water plant. In this invention, the flocculant, with or without the cationic polymer aid, and the acidified copper salt solution are thoroughly mixed in a processing vessel or tank by agitation, air mixing or a recirculating pump. The complete homogenous mixture is then loaded into the tank truck for delivery to the water plant. In an alternate production method, the flocculant, with or without the cationic polymer aid, is simultaneously loaded with the acidified copper salt solution into the tank of a tank truck. Final mixing occurs during transport, caused by agitation of the liquid contents due to movement of the truck.

The algicide-flocculant solution, with or without the polymeric flocculant aid, is added to raw water in the clarifier using conventional metering equipment to deliver sufficient flocculant to coagulate the particulates in the raw water. Typically, nearly saturated flocculant is added to the raw water in the range of 20–60 ppm, an average value being about 30 ppm. Because incoming raw water contains very little soluble copper, the active copper concentration in the clarifier is due almost entirely to the copper algicide combined with the flocculant. Thus, the clarifier water has a copper concentration in the range of 0.050–0.15 ppm.

Examples of this invention are:

EXAMPLE 1

Approximately 55 gallons of tap water are added to a mix tank. The water is then heated slightly using an electric immersion heater. 220 pounds of commercially available blue vitriol crystals are added to the mix tank and agitated vigorously with a powered impeller. During the mixing process, two-three gallons of 47–50% aluminum sulfate solution are added to the tank and mixing continues until the blue vitriol crystals are completely dissolved, producing a clear blue liquid. A processing vessel or tank is filled with 4000 gallons of 47–50% aluminum sulfate solution with no polymer flocculant aid. The copper sulfate solution is then transferred into the processing vessel or tank containing with the aluminum sulfate. This produces a solution of ½% by weight copper sulfate, 45–47% aluminum sulfate, balance water. After delivery to the water plant, the solution is transferred to a storage tank and then metered into the clarifier at about 30 ppm where it mixes substantially uniformly with the incoming raw water to flocculate particulates in the raw water and kill algae in the clarifier. In this example, the water plant had run 1% concentrations of copper sulfate in the flocculant to bring an algae bloom under control and the ½% solution in this batch was intended as a maintenance dosage to prevent recurrence of the algae bloom.

EXAMPLE 2

440 pounds of blue vitriol crystals are thoroughly dissolved in 110 gallons of tap water acidified with aluminum sulfate. The copper sulfate solution is added to 4000 gallons of 48–50% aluminum sulfate to produce a 1% copper sulfate solution. The algicide-flocculant solution is metered into the clarifier of a water plant at a dosage of about 30 ppm.

EXAMPLE 3

440 pounds of blue vitriol crystals are thoroughly dissolved in 110 gallons of tap water and acidified with aluminum sulfate. The copper sulfate solution is added to a 4000 gallon mixture of 41% liquid alum and 5% cationic polymeric flocculant aid, to provide a 1% copper sulfate solution having 0.25% active copper. The algicide-flocculant solution is metered into the clarifier of a water plant at a dosage of about 25 ppm.

EXAMPLE 4

300 pounds of cupric chloride dihydrate crystals are fully dissolved in 110 gallons of tap water, acidified with aluminum sulfate. This copper chloride solution is added to a 4000 gallon mixture of 46% aluminum sulfate and 1% cationic polymeric flocculant aid, to make a 0.68% copper chloride solution having 0.25% active copper.

EXAMPLE 5

490 pounds of blue vitriol crystals are completely dissolved in 110 gallons of tap water and acidified with liquid ferric sulfate. This copper sulfate solution is added to 3700 gallons of 38–42% liquid ferric sulfate, balance water, to make a 1% copper sulfate solution having 0.25% active copper.

EXAMPLE 6

245 pounds of blue vitriol crystals are thoroughly dissolved in 110 gallons of tap water and acidified with liquid ferric sulfate. This copper sulfate solution is added to a 3700 gallon mixture of 38% ferric sulfate and 2% cationic polymeric flocculant aid, to produce a 0.5% copper sulfate solution having 0.125% active copper.

EXAMPLE 7

335 pounds of copper chloride dihydrate are fully dissolved in 110 gallons of tap water and acidified with liquid ferric chloride. The copper chloride solution is added to 4100 gallons of 34–37% liquid ferric chloride, to make a 0.68% copper chloride solution having 0.25% active copper.

EXAMPLE 8

2200 pounds of blue vitriol crystals are thoroughly dissolved in 550 gallons of tap water, and acidified with aluminum sulfate. The copper sulfate solution is added to a 3475 gallon mixture of 25% liquid alum, 10% cationic polymeric flocculant aid, balance water, to provide a 5% copper sulfate solution having 1.25% active copper.

It is hard to exaggerate the effectiveness of the algicide-flocculant treatment of this invention in combating algae growth. For example, in one application in South Texas, the water plant had battled an algae bloom using the standard scattering of blue vitriol pellets into the clarifier for several months. Numerous complaints of bad tasting and bad smelling water were received. Upon using a 1% copper sulfate-aluminum sulfate solution of this invention, the bloom was over in a few days and complaints of bad taste and bad smell stopped.

Another, more objective, measure of the effectiveness of this invention is found by comparing copper concentrations in clarifier water and in tap water. In the examples in Table II, a copper sulfate-aluminum sulfate solution has been metered into a municipal plant clarifier in accordance with this invention. Substantially no copper is present in the raw water so all of the copper in the clarifier is added by this invention. No free copper is accumulating in the clarifier sludge. In other words, the copper consumed in the clarifier is being used for its intended purpose, i.e. to control algae growth. Table II tabulates the results of trace copper analyses on tap and clarifier water in several South Texas municipal water plants.

TABLE II

| location | date | Cu conc. in clarifier water, mg/L | Cu conc. in tap water, mg/L | Cu consumed in clarifier, mg/L | % Cu consumed in clarifier |
|---|---|---|---|---|---|
| plant S | 10/8/96 | 0.035 | 0.011 | 0.024 | 66% |
| plant L | 10/10/96 | 0.045 | 0.035 | 0.010 | 22% |
| plant D | 10/10/96 | 0.026 | 0.018 | 0.008 | 31% |
| plant O | 10/11/96 | 0.043 | 0.026 | 0.017 | 40% |

Upon reflection, it will be appreciated that the percentage of copper consumed in the clarifier is very high. The copper present in the clarifier water is very dilute. For the copper ion to replace the magnesium ion in chlorophyll, the ions must come very close together, the exact distance being measured in Angstroms. Even so, a significant part of the copper added to the clarifier by the technique of this invention is effective in combating algae.

It will also be appreciated that the reported percentage of copper consumed in the clarifier is understated because the measured copper concentration in the clarifier is not necessarily the same as the copper added to the clarifier. It is highly likely that some copper is consumed by algae in the clarifier before the water sample is taken that produces the results in Table II. Thus, the amount of reported copper in the clarifier is always less than the amount of copper added to the clarifier. The result is that the reported percentage of copper consumed in the clarifier is conservative.

Although this invention has been disclosed and described in its preferred forms with a certain degree of particularity, it is understood that the present disclosure of the preferred forms is only by way of example and that numerous changes in the proportion of the materials and the details of mixing and use may be resorted to without departing from the spirit and scope of the invention as hereinafter claimed.

What is claimed is:

1. A method of controlling algae in a municipal water plant, comprising the steps of:

passing raw water to a clarifier; and adding an effective amount of an algicide-flocculant solution to the clarifier, where the algicide-flocculant solution is mixed substantially uniformly with the incoming raw water, wherein (i) the algicide-flocculant solution comprises 25–50 wt % acidic flocculant, 0–10 wt % polymer flocculant aid, an algicide consisting essentially of copper having a concentration of 0.025–1.25 wt % in the form of a water soluble copper salt, balance water, and (ii) said effective amount of the algicide-flocculant solution is an amount sufficient to kill algae in the clarifier and to coagulate and/or flocculate particulates in the raw water that is in the clarifier.

2. The method of claim 1 wherein the water soluble copper salt is selected from the group consisting of copper sulfate, copper chloride, copper nitrate and copper acetate.

3. The method of claim 1 wherein said step of adding an effective amount of an algicide-flocculant solution to the clarifier is a step of adding an effective amount of a first batch of an algicide-flocculant solution in response to an algae bloom in the clarifier and the algicide-flocculant solution in the first batch comprises 25–50 wt % acidic flocculant, 0–10 wt % polymer flocculant aid, an algicide consisting essentially of copper having a concentration of 0.25–1.25 wt % in the form of a water soluble copper salt, balance water, and further comprising the step of subsequently adding, after the algae bloom has subsided in response to the first batch of the algicide-flocculant solution, an effective amount of a second batch of the algicide-flocculant solution to the clarifier and substantially uniformly mixing the second batch of the algicide-flocculant solution with the raw water in the clarifier, the second batch of the algicide-flocculant solution comprising 25–50 wt % acidic flocculant, 0–10 wt % polymer flocculant aid, an algicide consisting essentially of copper having a concentration that is substantially less than the copper concentration in the first batch of the algicide-flocculant solution, balance water, wherein the effective amount of the second batch of the algicide-flocculant solution is an amount sufficient to further control algae and coagulate and/or flocculate particulates in the raw water that is in the clarifier.

4. The method of claim 3, further comprising adding, after said further control of algae has been obtained with the second batch of the algicide-flocculant solution, an effective amount of a third batch of an algicide-flocculant solution to the clarifier and substantially uniformly mixing the third batch of the algicide-flocculant solution with the raw water in the clarifier, the third batch of the algicide-flocculant solution comprising 25–50 wt % acidic flocculant, 0–10 wt % polymer flocculant aid, an algicide consisting essentially of copper having a concentration that is substantially less than the copper concentration in the second batch of the algicide-flocculant solution, balance water, wherein the effective amount of the third batch of the algicide-flocculant solution is an amount sufficient to keep algae under control.

5. The method of claim 4, wherein the copper concentration in the first batch is 0.25–1.25 wt %, the copper concentration in the second batch is substantially less than about 0.25 wt %, and the copper concentration in the third batch is in the range of about 0.025–0.050 wt %.

6. A method of controlling algae in a municipal water plant, comprising the steps of pre-mixing an algicide-flocculant solution comprising 25–50 wt % acidic flocculant, 0–10 wt % polymer flocculant aid, an algicide consisting essentially of copper having a concentration of 0.025–1.25 wt % in the form of a water soluble copper salt, balance water; passing raw water to a clarifier; and adding an effective amount of the pre-mixed algicide-flocculant solution to the clarifier, where the premixed algicide-flocculant solution is mixed substantially uniformly with the incoming raw water, said effective amount of the algicide-flocculant solution being an amount sufficient to kill algae in the clarifier and to coagulate and/or flocculate particulates in the raw water that is in the clarifier.

7. The method of claim 6, wherein the water soluble copper salt is selected from the group consisting of copper sulfate, copper chloride, copper nitrate and copper acetate.

8. The method of claim 6, wherein a first batch of the premixed algicide-flocculant solution with a copper concentration of 0.25–1.25 wt % is added to the clarifier in response to an algae bloom in the clarifier to thereby obtain subsidence of the algae bloom.

9. The method of claim 8, further comprising the step of subsequently adding, after the algae bloom has subsided in response to the first batch of the algicide-flocculant solution, an effective amount of a second batch of the algicide-flocculant solution to the clarifier and substantially uniformly mixing the second batch of the algicide-flocculant solution with the raw water in the clarifier, the second batch of the algicide-flocculant solution comprising 25–50 wt % acidic flocculant, 0–10 wt % polymer flocculant aid, an algicide consisting essentially of copper having a concentration that is substantially less than the copper concentration in the first batch of the algicide-flocculant solution, balance water, wherein the effective amount of the second batch of the algicide-flocculant solution is an amount sufficient to further control algae and coagulate and/or flocculate particulates in the raw water that is in the clarifier.

10. The method of claim 9, further comprising adding, after said further control of algae has been obtained with the second batch of the algicide-flocculant solution, an effective amount of a third batch of an algicide-flocculant solution to the clarifier and substantially uniformly mixing the third batch of the algicide-flocculant solution with the raw water in the clarifier, the third batch of the algicide-flocculant solution comprising 25–50 wt % acidic flocculant, 0–10 wt % polymer flocculant aid, an algicide consisting essentially of copper having a concentration that is substantially less than the copper concentration in the second batch of the algicide-flocculant solution, balance water, wherein the effective amount of the third batch of the algicide-flocculant solution is an amount sufficient to keep algae under control.

11. The method of claim 10, wherein the copper concentration in the first batch is 0.25–1.25 wt %, the copper concentration in the second batch is substantially less than about 0.25 wt %, and the copper concentration in the third batch is in the range of about 0.025–0.050 wt %.

* * * * *